United States Patent [19]

Alpert et al.

[11] 3,989,734

[45] Nov. 2, 1976

[54] SLURRY PHASE METHANATION PROCESS

[75] Inventors: Seymour Bernard Alpert, Los Altos, Calif.; Martin Barry Sherwin, Wayne, N.J.; Neal Paul Cochran, Frederick, Md.

[73] Assignee: The United States of America as represented by the Secretary of State, Washington, D.C.

[22] Filed: Oct. 25, 1974

[21] Appl. No.: 518,036

Related U.S. Application Data

[63] Continuation of Ser. No. 327,245, Jan. 26, 1973, abandoned.

[52] U.S. Cl. .................. 260/449.6; 260/449 L; 48/197 R
[51] Int. Cl.² .................. C07C 1/04; C07C 1/16
[58] Field of Search ............... 260/449.6 M, 449 L, 260/449.6, 449 R

[56] References Cited
UNITED STATES PATENTS

| 2,433,255 | 12/1947 | Atwell | 260/449 L |
|---|---|---|---|
| 2,438,029 | 3/1948 | Atwell | 260/449 L |
| 2,671,103 | 3/1954 | Kolbel et al. | 260/449 L |
| 2,692,274 | 10/1954 | Kolbel et al. | 260/449 L |
| 2,775,607 | 12/1956 | Kolbel et al. | 260/449 L |
| 2,852,350 | 9/1958 | Kolbel et al. | 260/449 L |

FOREIGN PATENTS OR APPLICATIONS

| 167,059 | 2/1956 | Australia | 260/449 L |
|---|---|---|---|
| 787,122 | 12/1957 | United Kingdom | 260/449 L |
| 780,880 | 8/1957 | United Kingdom | 260/449 L |

*Primary Examiner*—Howard T. Mars
*Attorney, Agent, or Firm*—Bert J. Lewen

[57] ABSTRACT

A gas stream containing carbon monoxide and hydrogen is methanated by passing the gas stream upwardly through a suspension of a finely divided hydrogenation catalyst in a fluidizing medium. The reaction takes place at a temperature of from 450 to 950° F.

3 Claims, 1 Drawing Figure

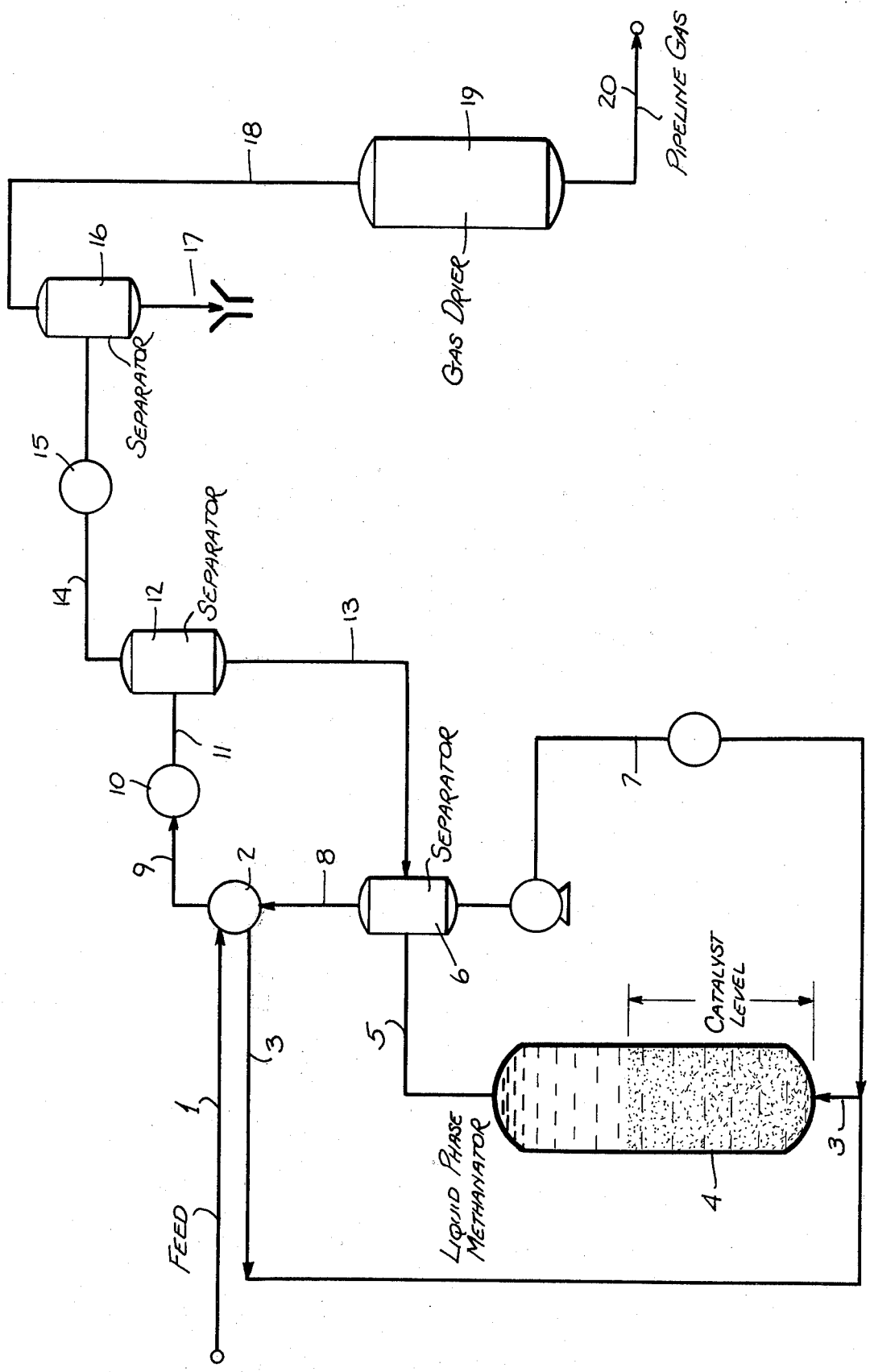

SLURRY PHASE METHANATION PROCESS

This is a continuation of application Ser. No. 327,245, filed Jan. 26, 1973 now abandoned.

DETAILED DESCRIPTION OF THE INVENTION

This invention relates to a new and improved process for the methanation of product gases containing carbon monoxide and hydrogen. More specifically, the invention teaches a methanation process employing a slurry phase fluidized bed system.

In coal and heavy hydrocarbon gasification, the product gases contain significant amounts of carbon monoxide and hydrogen and relatively low amounts of methane. In order to manufacture pipeline gas with 1000 BTU per cubic foot heating value, the carbon monoxide and hydrogen must be converted to methane. Since carbon monoxide is toxic, its content in pipeline gas must be reduced to 0.1% or less. Methanation is the process step used for this conversion.

Methanation for making pipeline gas is not yet a commercial process. To date, process development efforts to convert carbon monoxide to methane have involved fixed bed gas phase systems.

The major problem in gas phase methanation is to control and design the reaction system for the removal of the heat released. This is particularly difficult due to the highly exothermic nature of the carbon monoxide-hydrogen reaction. About 100,000 BTU's are released per pound-mole of carbon monoxide converted. A second problem is to control the reaction temperature within an optimum range. The methanation reaction rate is low below 500° F., while above 850° F. catalyst life is decreased and carbon deposition can occur, deleteriously affecting catalyst life. In addition, at high temperatures, the methanation reaction reverses so that conversion to methane is reduced. A third problem is to minimize pressure drop across the reactors without inordinately increasing catalyst particle size (and decreasing catalyst surface area).

To overcome these problems of the gas phase methanation many design features have been proposed: These include the introduction of cold feed gas between stages and at quench points in the reactor and recycling large quantities of product gas to lower the concentration of carbon monoxide at the reactor inlet. These modifications, however, have not been entirely satisfactory because only a limited amount of heat can be taken up in the feed gas and, where recycle is used, high operating costs are necessary to circulate, cool, reheat and recompress the recycled product gas.

Additional drawbacks to the gas phase process designs are gas distribution, complex reactor systems and the need for a complicated array of heat exchange equipment. In the case of fixed bed designs, large size catalyst particles are required to minimize pressure drop. This results in a high temperature rise across the reactor (on the order of 300° F.) and non-optimum reaction conditions over most of the reactor.

While gas phase fluid bed systems have been proposed and studied to overcome these problems, catalyst attrition is found to be a process difficulty difficult to circumvent.

In accordance with the invention, it has now been discovered that methanation can be performed without the several disadvantages described above by employing an upwardly moving liquid fluid bed of relatively high boiling hydrocarbons.

The liquid hydrocarbon serves to fluidize the active small sized methanation catalyst and as a heat carrier "fly wheel" wherein the heat of hydrogenation of carbon monoxide is taken up by direct contact. The sensible heat and heat of vaporization of the fluidizing oil media, the cold feed gas and recycled liquid provide a heat sink. Isothermal operation of the reaction system is readily achieved by having the catalyst particles in an expanded state and absorbing the exothermic heat with the cool feed gas and cooled liquid recycle streams.

Advantages of the liquid fluidized system are manifold:

1. Reactor design is simplified. Liquids and gases are readily distributed across the reactor cross-sectional area without the necessity for redistribution and quench along the reactor length.

2. Heat control of exothermic hydrogenation reactions is excellent; the reactors are nearly isothermal with a temperature spread of only 5°–10° F. between inlet and outlet.

3. Vapor-liquids can be disengaged without pressure let down.

4. Small size catalyst can be used, thereby achieving higher rates of reaction than with large catalyst particles.

5. Catalyst can be added and withdrawn from the system without the necessity to remove spent catalyst or to "swing" the reaction systems from on-stream operations to regeneration. Regeneration, if needed, is accomplished in external equipment.

6. The isothermal temperature of the system permits optimum conditions favoring the desired reaction kinetics.

7. Catalyst activity can be maintained at a constant "equilibrium" activity level so that it is not necessary to overdesign the reactor size for the poorest catalyst activity level.

In one alternate, a bed of particulate catalyst can be fluidized and retained in the reactor without carry-over of catalyst particles. Alternatively, catalyst and liquids can be carried overhead with the liquid, through the heat exchangers and recycled.

Unlike gas-solid fluidized methanation systems, attrition of methanation catalyst is not a process difficulty because of the relatively low velocities in the liquid fluidized bed. The catalyst is also cushioned by the fluidized oil media.

In contrast to fixed bed gas phase methanation processes, pressure drop across the bed is not a restricting design factor because the large quantities of gas necessary to limit the carbon monoxide concentration in the feed to low levels are not required; since higher inlet concentrations of carbon monoxide are permissible.

The FIGURE is a flow sheet showing the liquid phase methanation process of the invention. In this embodiment the fluidized catalyst is not carried overhead with the liquid.

A purified gasified effluent feed containing 75% hydrogen and 25% carbon monoxide is feed to the methanation process via line 1, passed through the heat exchange 2, thereby increasing its temperature to 1000° F., and thereafter feed via line 3 to the liquid phase methanator 4. The methanator has a diameter of 10 feet and a height of 25 feet. The total pressure therein is 1000 psig, the superficial gas velocity 0.2 feet per second, and the space velocity 800 SCF of gas per hour, SCF of reactor.

The reactor effluent is withdrawn from the liquid phase methanator 4 via line 5 and sent to separator 6. In separator 6 the liquid and vapor effluent is divided, the liquid being pumped out of the bottom of the separator and recycled, after cooling (not shown), back to the bottom of the liquid phase methantor 4 via line 7. The gaseous product is removed from the separator 6 via the line 8 and heat exchanged with the effluent feed in heat exchanger 2. The cool vapor is then passed through cooler 10 via line 9, and then via line 11, to separator 12. In separator 12 the liquid formed upon cooling is separated from the bottom via line 13 and recycled to the separator 6. The remaining vapor is withdrawn overhead via line 14, subject to further cooling in cooler 15 and separated again in separator 16. Additional water is withdrawn and collected via line 17 while the remaining vapor is passed via line 18 to the gas dryer 19. The gas dryer contains silica gel and serves to remove the last traces of moisture from the feed stock. The dried gas is removed via line 20 wherein there is recovered 50 million standard cubic feet of pipeline gas having 92.4% of methane, 1.9% carbon monoxide and 5.7% hydrogen.

The catalyst in the liquid fluidized bed is 59 weight percent nickel oxide and 41% kieselguhr which serves as the catalyst support. The catalyst is in the form of an extrudate having a diameter of 0.032 inches and a length of 0.25 inches. The oil is a desulfurized heavy gas oil, 25° API; having 0.01 weight % sulfur and a boiling range of 650° to 1100° F. The oil velocity in the reactor is 30 gallons per minute per square foot of reactor cross-section.

The aforesaid example, while setting forth a preferred embodiment of the invention, is merely exemplary. The feed composition may be from 1.0 to 25% carbon monoxide and from 3.0 to 75% hydrogen. Preferably, the feed contains from about 5.0 to 20% carbon monoxide and from about 15.0 to 60% hydrogen.

The space velocity may range from 500 to 50,000 SCF/CF reactor-hours. Preferably from 1,000 to 10,000 SCF/CF reactor-hours. The temperature may range from 450° to 950° F., preferably, though, 500° to 800° F.

In addition to the nickel type hydrogenation catalyst shown in the example, iron, cobalt, molybdenum, rhenium and other noble metals on heterogeneous supports may be used. Preferably, nickel and promoted nickel catalysts are selected. Any chemically inert support having a low attrition may be used. Examples of these are kieselguhr, alumina, silica-alumina, zirconia, silicon carbide and carbon. The catalyst is in the form of an extrudate, from 3/8 inch to 100 mesh (150 microns) in a spherical or granular form. This particle size is equivalent to 0.006 to 0.375 inches.

The liquid fluidizing medium must be chemically stable and liquid under the reaction conditions. Preferably it is sulfur-free (especially if the catalyst is poisoned by sulfur). Examples of suitable fluidizing media are mineral oils such as Penndrake code 4417 and Sun 21 (a trademark of Sun Oil Company); paraffinic compounds having a boiling range of from 400° F. to 1000° F.; desulfurized gas oils, silicone oils, and liquid polymers of tetrafloroethylene. The velocity of the liquid fluidizing medium is dependent on the physical characteristice of the extrudate catalyst. For example, if a 3/8 inch catalyst is used, the velocity should be from 60 to 100 gpm/ft$^2$. For the finer catalysts, such as the 100 mesh type, from 2 to 10 gallon gpm/ft$^2$. is sufficient. As a general rule, the liquid flow should be sufficient to expand the bed by at least 5% as compared to its settled state, preferably not more than 30%.

The advantages of the invention over the fixed bed type process can be readily seen by the following comparative example:

The same feed gas and operating conditions shown in the above example are used, except the fixed bed catalyst is in the form of a tablet 1/4 inch × 1/4 inch, the catalyst loading is 0.385 pounds, and the catalyst space velocity is 130 SCF/Hr pounds catalyst. The analysis of the product gas (on a dry basis) shows only 85.6% methane, 10.8% hydrogen and 3.6% carbon monoxide. This increased level of carbon monoxide is particularly striking and evidences clearly the advantage of the process of the invention.

We claim:

1. A process for converting a gas stream containing from 1 to 25 mole % of carbon monoxide and from 2 to 75 mole % of hydrogen to methane which comprises: passing said gas stream and a fluidizing medium which is a chemically stable liquid selected from the group consisting of desulfurized gas oils and paraffins having a boiling point of from 400° to 1000° F. into a reaction zone containing a bed of nickel catalyst particles; maintaining a flow rate of such gas stream and fluidizing medium upwardly through said reaction zone so as to expand the volume of said bed of nickel catalyst particle by at least 5% at a temperature of from 500° to 800° F., said nickel catalyst particles having a particle size of from 0.006 to 0.375 inches.

2. The process of claim 1 wherein the nickel catalyst is in the form of an extrudate.

3. The process of claim 1 wherein the space velocity in said reaction is from 500 to 50,000 SCF/CF-hours.

* * * * *